(12) United States Patent
Westerhoff et al.

(10) Patent No.: US 12,193,855 B2
(45) Date of Patent: Jan. 14, 2025

(54) METHOD AND SYSTEM FOR RULE BASED DISPLAY OF SETS OF IMAGES

(71) Applicant: PME IP PTY LTD, Richmond (AU)

(72) Inventors: Malte Westerhoff, Berlin (DE); Detlev Stalling, Berlin (DE)

(73) Assignee: PME IP PTTY LTD, Richmond (AU)

( * ) Notice: Subject to any disclaimer, the term of this patent is extended or adjusted under 35 U.S.C. 154(b) by 26 days.

(21) Appl. No.: 18/209,692

(22) Filed: Jun. 14, 2023

(65) Prior Publication Data

US 2023/0320678 A1    Oct. 12, 2023

Related U.S. Application Data

(63) Continuation of application No. 17/485,864, filed on Sep. 27, 2021, now Pat. No. 11,701,064, which is a
(Continued)

(51) Int. Cl.
*G06T 11/00* (2006.01)
*A61B 5/055* (2006.01)
(Continued)

(52) U.S. Cl.
CPC .............. *A61B 6/032* (2013.01); *A61B 5/055* (2013.01); *A61B 6/037* (2013.01); *A61B 6/465* (2013.01); *A61B 6/466* (2013.01); *G06T 11/001* (2013.01); *G06T 15/08* (2013.01); *G06T 19/20* (2013.01); *G09G 5/363* (2013.01); *G16H 30/20* (2018.01); *G16H 30/40* (2018.01); *G16H 50/70* (2018.01); *G06F 3/0481* (2013.01);
(Continued)

(58) Field of Classification Search
CPC ....... G06T 15/08; G06T 11/001; G06T 11/60; G06T 19/20; G06T 2200/04; G06T 2200/24; G06T 2210/41; G06T 219/9012; G06T 2219/2024; G16H 30/20; G16H 50/70; G16H 30/40; G06F 19/00; G06F 3/0481; G06F 3/216254; G09G 5/363; A61B 5/055; A61B 5/7475; A61B 6/032; A61B 6/037; A61B 6/645; A61B 6/466; A61B 5/5205; A61B 5/08
See application file for complete search history.

(56) References Cited

U.S. PATENT DOCUMENTS 6,765,570 B1    7/2004    Cheung
10,762,872 B2    9/2020    Westerhoff
(Continued)

OTHER PUBLICATIONS

Higgins et al., Distributed System for Processing 3D Medical Images, Compat Biol Med (1997) 27, pp. 97-115.
(Continued)

*Primary Examiner* — Wesner Sajous
(74) *Attorney, Agent, or Firm* — SCI-LAW STRATEGIES PC

(57) ABSTRACT

The invention provides, in some aspects, a system for implementing a rule derived basis to display image sets. In various embodiments of the invention, the selection of the images to be displayed, the layout of the images, as well as the rendering parameters and styles can be determined using a rule derived basis. In an embodiment of the present invention, the user is presented with images displayed based on their preferences without having to first manually adjust parameters.

20 Claims, 3 Drawing Sheets

Related U.S. Application Data continuation of application No. 16/913,839, filed on Jun. 26, 2020, now Pat. No. 11,129,578, which is a continuation of application No. 16/446,546, filed on Jun. 19, 2019, now Pat. No. 10,762,687, which is a continuation of application No. 15/870,681, filed on Jan. 12, 2018, now Pat. No. 10,373,368, which is a continuation of application No. 15/380,848, filed on Dec. 15, 2016, now Pat. No. 9,898,855, which is a continuation of application No. 14/611,163, filed on Jan. 30, 2015, now Pat. No. 9,524,577, which is a continuation of application No. 13/831,975, filed on Mar. 15, 2013, now Pat. No. 8,976,190.

(51) Int. Cl.
| | | |
|---|---|---|
| *A61B 6/03* | (2006.01) | |
| *A61B 6/46* | (2024.01) | |
| *G06F 3/048* | (2013.01) | |
| *G06T 15/08* | (2011.01) | |
| *G06T 19/20* | (2011.01) | |
| *G09G 5/36* | (2006.01) | |
| *G16H 30/20* | (2018.01) | |
| *G16H 30/40* | (2018.01) | |
| *G16H 50/70* | (2018.01) | |
| *G06F 3/0481* | (2022.01) | |

(52) U.S. Cl.
CPC ...... *G06T 2200/04* (2013.01); *G06T 2210/41* (2013.01); *G06T 2219/2012* (2013.01); *G06T 2219/2024* (2013.01)

(56) References Cited

U.S. PATENT DOCUMENTS

| | | |
|---|---|---|
| 11,514,572 B2 | 11/2022 | Westerhoff |
| 11,599,672 B2 | 3/2023 | Stalling |
| 11,620,773 B2 | 4/2023 | Westerhoff |
| 11,640,809 B2 | 5/2023 | Westerhoff |
| 11,763,516 B2 | 9/2023 | Westerhoff |
| 2006/0149850 A1 | 7/2006 | Bowman |
| 2008/0052126 A1 | 2/2008 | Sasai |
| 2008/0123917 A1* | 5/2008 | Magsig ................. G06T 7/0014 382/128 |
| 2008/0166070 A1* | 7/2008 | Kariathungal ......... G16H 30/40 382/305 |
| 2014/0173287 A1 | 6/2014 | Mizunuma |
| 2017/0032546 A1 | 2/2017 | Westerhoff |
| 2020/0327669 A1 | 10/2020 | Westerhoff |
| 2020/0366614 A1 | 11/2020 | Stalling |
| 2021/0256742 A1 | 8/2021 | Westerhoff |
| 2021/0352133 A1 | 11/2021 | Westerhoff |
| 2022/0165231 A1 | 5/2022 | Westerhoff |
| 2023/0195937 A1 | 6/2023 | Stalling |
| 2023/0260478 A1 | 8/2023 | Westerhoff |

OTHER PUBLICATIONS

Au2022200601, Office Action, dated Dec. 8, 2022, 4 pages.
AU2018335370, Office Action, dated May 15, 2023, 4 pages.
CA2991378, Office Action, dated Oct. 24, 2022, 7 pages.
CA2991378, Office Action, dated Oct. 20,2023, 8 pages.
EP3329405, Summons, dated Jul. 7, 2023, 14 pages.
EP202303856_OA_Aug. 23, 2023, 7 pages.
JP2022-191827, Office Action, dated Oct. 18, 2023, 2 pages (& English translation).

* cited by examiner

Figure 3

List of Auto-Prior Rules
- Prior Chest CR

Auto-Prior Rule Properties

Name: Prior Chest CR
User Levels:
Comment: For any current chest study CR load prior CT or CR exams of the chest
Other: ☐ Disable  ☐ Overwrite system rule Current study must match all of the following:

| All of the following ⬍ |
|---|
| Modality ⬍ | Contains Any Of ⬍ | CR CT | + − |
| Any of the following ⬍ |
| Body Part Examined ⬍ | Equals ⬍ | CHEST | + − |
| Study Description ⬍ | Contains Any Of ⬍ | CHEST THORAX | + − |

Prior study must match all of the following:

| All of the following ⬍ |
|---|
| Modality ⬍ | Contains Any Of ⬍ | CR | + − |
| Any of the following ⬍ |
| Body Part Examined ⬍ | Equals ⬍ | CHEST | + − |
| Study Description ⬍ | Contains Any Of ⬍ | CHEST THORAX | + − |

○ System   ⊙ User

[New Rule] [Move to System] [Delete Rule] [Properties...]   [Save] [Cancel]

METHOD AND SYSTEM FOR RULE BASED DISPLAY OF SETS OF IMAGES

PRIORITY CLAIM

This application is a continuation of (1) U.S. application Ser. No. 17/485,864 filed Sep. 27, 2021 entitled "Method And System for Rule-Based Display of Sets of Images", inventors: Malte Westerhoff and D Stalling", which is a continuation of (2) U.S. application Ser. No. 16/913,839 filed Jun. 26, 2020 entitled "Method And System for Rule-Based Display of Sets of Images", inventors: Malte Westerhoff and D Stalling" and issued Sep. 28, 2021 as U.S. Pat. No. 11,129,578, which is a continuation of (3) U.S. application Ser. No. 16/446,546 filed Jun. 19, 2019 entitled "Method And System for Rule-Based Display of Sets of Images", inventors: Malte Westerhoff and D Stalling" and issued Jul. 16, 2020 as U.S. Pat. No. 10,762,687, which is a continuation of (4) U.S. application Ser. No. 15/870,681 filed Jan. 12, 2018 entitled "Method And System for Rule-Based Display of Sets of Images", inventors: Malte Westerhoff and D Stalling and issued Aug. 6, 2019 as U.S. Pat. No. 10,373,368 which is a continuation of (5) U.S. application Ser. No. 15/380,848 filed Dec. 15, 2016 entitled "Method And System for Rule-Based Display of Sets of Images", inventors: Malte Westerhoff and D Stalling and issued Feb. 20, 2018 as U.S. Pat. No. 9,898,855 which is a continuation of (6) U.S. application Ser. No. 14/611,163 filed Jan. 30, 2015 entitled "Method And System for Rule-Based Display of Sets of Images", inventors: Malte Westerhoff and D Stalling and issued Dec. 20, 2016 as U.S. Pat. No. 9,524,577 which is a continuation of (7) U.S. application Ser. No. 13/831,967, entitled "Method And System for Rule-Based Display of Sets of Images", inventors M. Westerhoff et al, which was filed Mar. 15, 2013 and issued Mar. 10, 2015 as U.S. Pat. No. 8,976,190, where (1) through (7) are herein expressly incorporated by reference in their entireties.

BACKGROUND OF THE INVENTION

In order to diagnose a traditional X-Ray examination, the images printed on films would be 'hung' in front of a light box. For multi-image examinations, as well as for comparison with priors, the 'hanging' would often follow a specific protocol. For example, a particular organization or doctor may choose for a two-view chest X-Ray with a two-view prior exam, that the films be hung from left to right as follows: Frontal view of current examination, lateral view of current examination, frontal view of prior examination, lateral view of prior examination. In contrast, the doctor may hang mammography exams with the corresponding views of current and prior next to each other, if that was more appropriate for the diagnostic workflow in that case. Thus, the organization or doctor developed a traditional 'Hanging Protocol'. Currently, the film and the light box are often being replaced by computer systems, called PACS (Picture Archiving and Communication System). PACS systems can mimic the Hanging Protocols.

Traditional X-Ray examinations typically produce one or a small number of single two dimensional (2D) images. In contrast, the more advanced imaging modalities such as Computer Tomography (CT), Magnetic Resonance Imaging (MRI) or Positron Emission Tomography (PET) can produce dozens of series, each consisting of a hundred or more images. It is possible and not uncommon to review images from these advanced modalities in the same manner as traditional X-Ray images, i.e., by hanging the individual images side-by-side, either on a light-box or using a PACS system.

SUMMARY OF THE INVENTION

The invention pertains to digital data processing and, more particularly, by way of example, to the visualization of image data. Three dimensional (3D) and four dimensional (4D) image data is routinely acquired with CT, MRI, PET, confocal microscopes, 3D ultrasound devices, and other imaging devices. The medical imaging market is just one example of a market that uses these devices. The visualization of image data market is growing rapidly, with new CT scanners collecting larger amounts of data more quickly than previous generation CT scanners. The invention has application to areas including medical imaging, atmospheric studies, astrophysics and geophysics.

With the rapid increase in the amounts and types of information that can be acquired using imaging technology, we have identified a substantial problem with integrating different types of image-based information into a form that can be used by a physician or diagnostician. Namely, although there may be many different types of image data, the forms, formats, integration, and display of relevant information is extremely difficult for a person to carry out without sophisticated computer processing. Embodiments of this invention therefore provide a computer-based analytic framework whereby image-based information from a variety of different sources can be integrated to provide increased ability to diagnose and evaluate a patient's condition. We have identified another substantial problem in the art, namely the increased likelihood of confusion of image-based information from different patients. In such situations, a physician or diagnostician may be presented with image-based information from different patients. Such inadvertent conflation can produce mis-diagnosis or mistaken non-diagnosis. In each case, the outcome for the patient can be serious, and can result in increased morbidity and mortality.

In general aspects of this invention, a First Study is first selected for review by a physician or diagnostician. Selection of a Study will generally be based on some particular characteristic. Such characteristic can be anatomical, disease-based, or both. Once a First Study is selected, an Additional Candidate Study can be selected based on the anatomical location of the First Study. Therefore, if the First Study is a Chest X-Ray, an Additional Candidate Study can be a Chest CT scan, MRI, positron-emission tomography (PET) scan, or other image of the chest. Alternatively, if a First Study is an X-Ray image of the gastrointestinal tract, an Additional Candidate Study could be a series of X-Ray images taken after ingestion of a contrast agent (such as barium). It can be appreciated that such anatomically selected Additional Candidate Studies can be applied to any organ, organ system, or tissue.

Alternatively, Additional Candidate Studies can be selected based on the type of disorder of disease being evaluated. For example, in a case in which a patient has had a diagnosis of cancer of one organ (e.g., lung), it can be desirable for Additional Candidate Studies to be targeted to identification of metastases in another organ. Thus, if a First Study is a Chest X-Ray, an Additional Candidate Study can be of the lymphatic system, head and neck, or various abdominal quadrants. Such Additional Candidate Studies may be X-ray, CT scans, MRI scans, PET scans, vascular visualizations (e.g., with injected contrast media) or histological images taken during a biopsy. Because the degree of detail (i.e., "granularity") obtained using different imaging techniques may vary widely it can be desirable to have a Rule Based process whereby the granularity of an Additional Candidate Study is increased over that of the First Study.

For example, a Chest X-Ray is a two-dimensional image in which the entirety of the chest and lungs is represented as a flat image. An Additional Candidate Study could be a CT scan, where "2-dimensional" images are acquired at a series of different "depths" (e.g., "slices") through the organ. If the 2-dimensional images are of sufficient quality to produce a 3-dimensional image of the organ with desirable degree of granularity, then the Additional Candidate Study can be depicted and displayed along with the image of the First Study.

General Rule 1 for selecting an Additional Candidate Study therefore can be:

IF (Primary.Dicom.BodyPartExamined) is "ANATOMICAL REGION 1", and (Primary.Dicom.Modality=IMAGE TYPE 1").

THEN SELECT other studies for loading, WHERE (Other.Dicom.BodyPart Examined=ANATOMICAL REGION 1") and (Other.Dicom.Modality="IMAGE TYPE 2").

If desired, in General Rule 1, Additional Candidate Studies can target "Other.Dicom.Modality="IMAGE TYPE 2").

It can be appreciated that any number of Additional Candidate Studies can be integrated using the computer-based processes of this invention.

Alternatively, General Rule 2 for selecting an Additional Candidate Study therefore can be:

IF (Primary.Dicom.Disease) is "DISEASE 1", and (Primary.Dicom.Modality=IMAGE TYPE 1")

THEN SELECT other studies for loading, WHERE (Other.Dicom.Disease)="DISEASE 1") and (Primary.Dicom.Modality="IMAGE TYPE 2").

It can be readily appreciated that application of General Rule 2 can integrate other Anatomical Regions and a number of different Image Types. It can also be appreciated that using "DICOM" in the rules, the likelihood of conflation of images from different patients can be substantially or completely eliminated.

Additionally, to consider information derived from different patients simultaneously, the selection for "DICOM" can be in a First Study, "DICOM 1" and THEN SELECT an image from "DICOM 2." Integrating this additional feature into a Rule Based computerized system can permit detection and analysis of disease "clusters" (e.g., cancer clusters; toxin-induced clusters, infection clusters, and the like).

In an embodiment of the present invention, a method or system uses a rule derived basis to display image sets. In various embodiments of the present invention, the selection of the images to be displayed, the layout of the images, i.e., the hanging, as well as the rendering parameters and styles can be determined using a rule derived basis. In an embodiment of the present invention, the user is presented with images displayed based on their preferences without having to first manually adjust parameters. Accordingly, there is a time saving in not displaying images initially in a non-rule derived basis.

These and other aspects of the invention are evident in the drawings and in the description that follows.

BRIEF DESCRIPTION OF THE DRAWINGS

This invention is described with respect to specific embodiments thereof.

Additional features can be appreciated from the Figures in which:

FIG. 3 shows an example of a user interface to specify rules including a dialog box to configure Study Selection rules, according to an embodiment of the invention.

DETAILED DESCRIPTION OF THE INVENTION

Definitions

Figure 1:
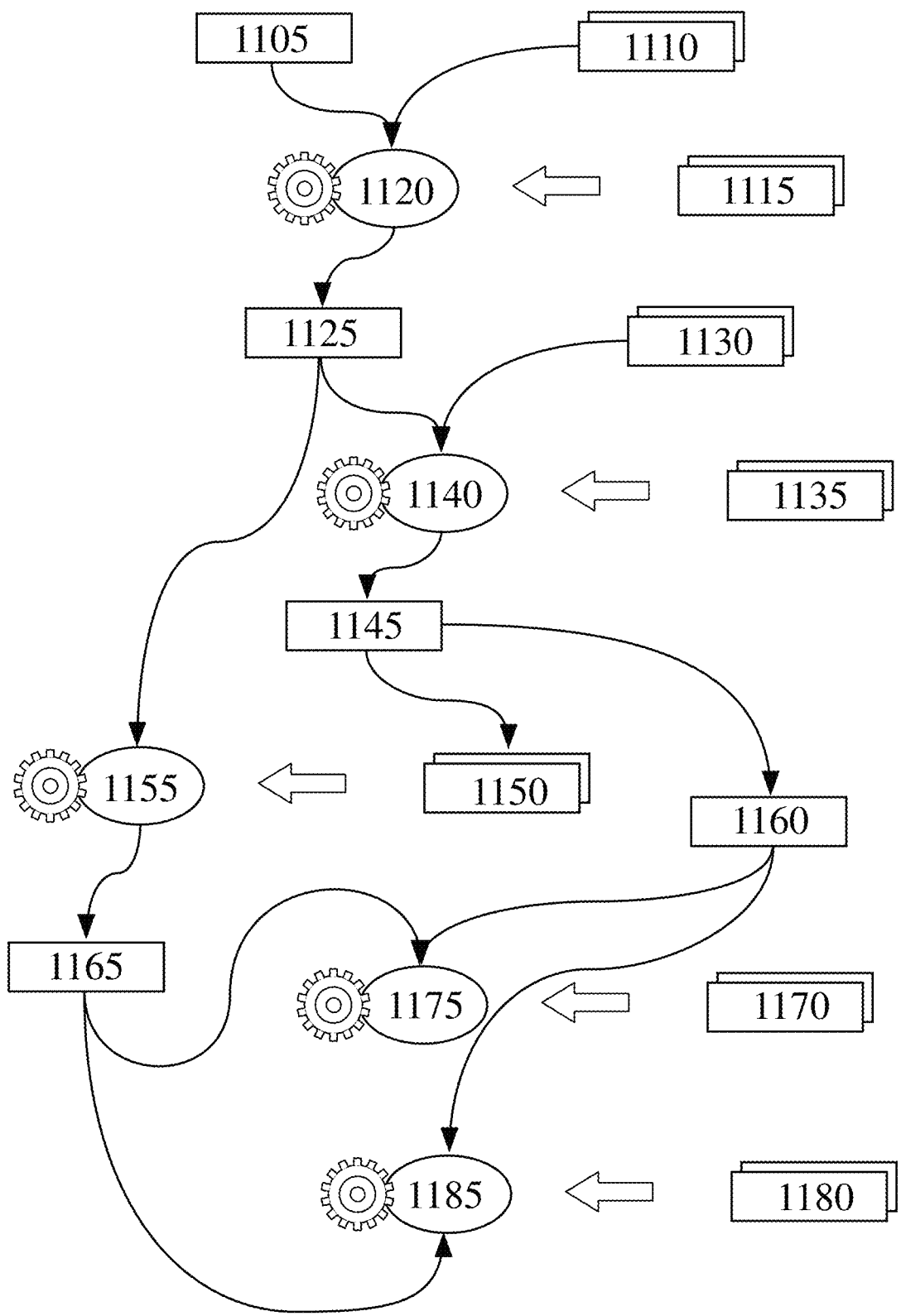
FIG. 1 depicts a flow chart showing the steps of applying various rules to the selected Study, according to an embodiment of the invention.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

The term "Study" will be used to refer to the set of images produced by an examination. A Study consists of one or more images. The images can be grouped into one or more image series. Each image, each series, and the whole Study can have different parameters attached. For medical images these can be defined by the Digital Imaging and Communication in Medicine (DICOM) standard.

The term "Hanging Protocol" will be used to refer to specific conventions how X-Ray films are arranged (hung) at a light box.

The term "Display Protocol" will be used to refer to the way images are displayed in a computer system, specifically the selection of the images to be displayed, the layout of the images, as well as the rendering parameters and styles.

The term "View" will be used to refer to data corresponding to a digital image view of a Set of Images rendered with a given set of rendering parameters and rendering modes.

The term "Viewport" will be used to refer to the logical part of the screen on the client computer in which a particular View is displayed, for example the user interface on the client computer can contain four rectangular Viewports 1160 of which three show a frontal, left, and bottom view respectively of a particular data, while the fourth viewer might show a 2D cross section through the same or a different data set.

The term "Sets of Images" or "Image Set" will be used to refer to one or more images, selected based on the rules.

The term "Study Selection Rules" will be used to refer to the rules used to select the studies to be displayed.

The term "Protocol Selection Rules" will be used to refer to the rules used to select the layout of the images to be displayed.

The term "Image Set Rules" will be used to refer to the rules used to form Image Sets 1165 from the images of one or more Study by applying selection, sorting, and breaking rules.

The term "Style Rules" will be used to refer to the rules to determine which rendering type, rendering style, and rendering parameters are used for a particular Image Set 1165 in a particular viewer.

The term "Volume Rendering" will be used to refer to Volume Rendering techniques including shaded Volume Rendering techniques, maximum intensity projection (MIP), oblique slicing or multi-planar reformats (MPR), axial/sagittal and coronal slice display, and thick slices (also called slabs). In medical imaging, for example, Volume Rendering is used to display 3D images from 3D image data sets, where a typical 3D image data set is a large number of 2D slice images acquired by a CT or MRI scanner and stored in a data structure.

Overview

Often, the traditional 'Hanging Protocol' is either not intuitive, cannot display the information in a manner in which it can be reviewed or is not the most efficient way to display images. Alternative ways of rendering the acquired images can be more efficient or more appropriate for displaying the information. Examples include Volume Rendering techniques or maximum intensity projections of stacks of cross-sectional images, rendering of oblique slices, rendering of thick slices or slabs, or rendering of fused images (e.g. in PET/CT). Specialized diagnostic workstations that are often specific to a clinical application area are used to provide appropriate rendering of the acquired images. As organizations and doctors require better and faster visualization methods that allow users to interact with the image data in real-time, the requirements and demands for displaying the data will increase.

Figure 2:
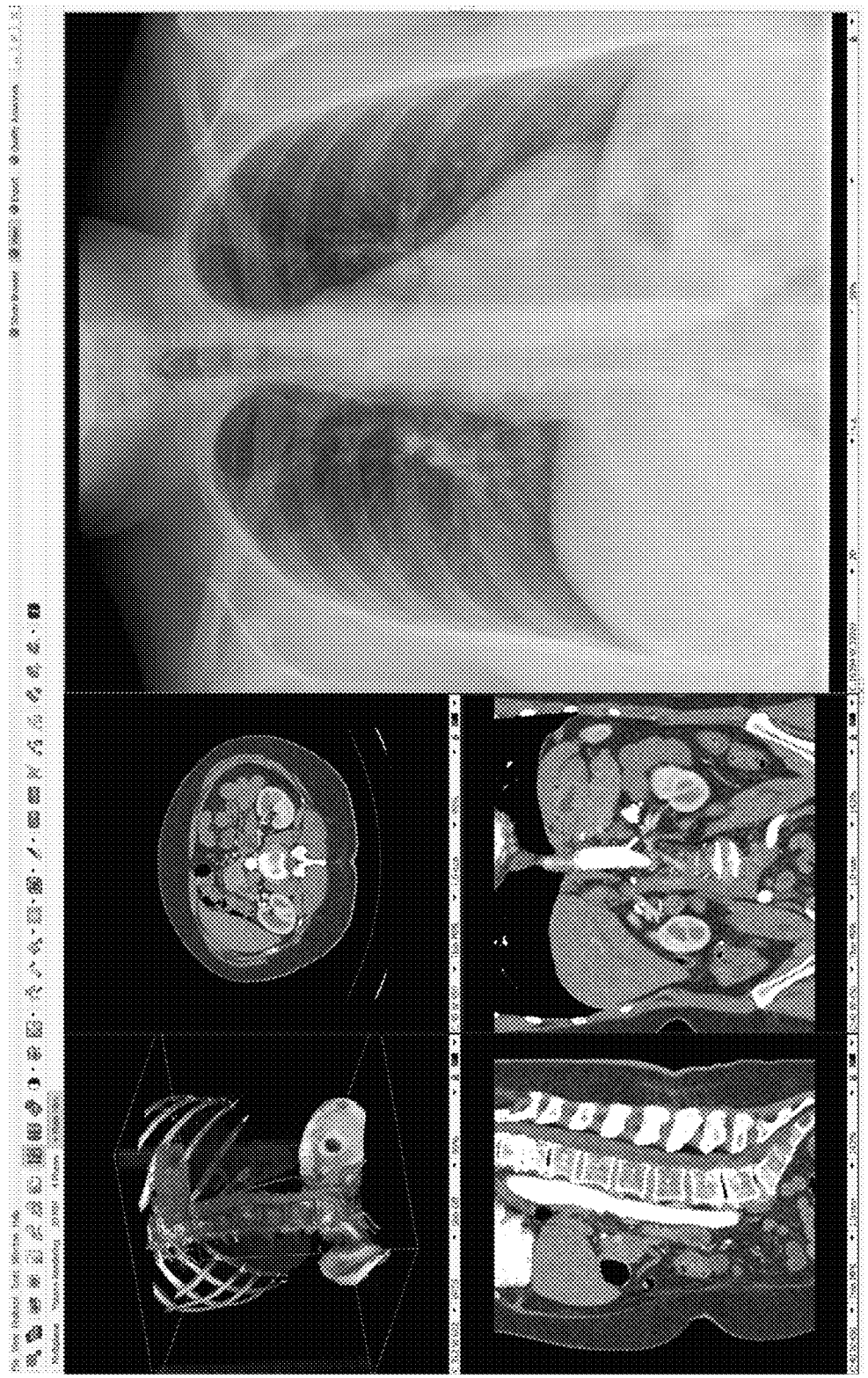
FIG. 2 depicts the resulting display for an example study, according to an embodiment of the invention.

FIG. 2 depicts an example study where the rules have created two Sets of Images. One Set of Images consists of a series of CT images forming a 3D volume, which is depicted in a volume rendered style in the Viewport 1160 in the upper left and in three orthogonal cross sections in the three other viewports in the left half of the screen. The second Set of Images consist of one chest X-Ray, assigned to a single Viewport 1160 covering the right half of the screen and rendering the X-Ray in 2D style. Appropriate data windows have been chosen by the rules to highlight the vasculature in the 3D rendering, as this is a study with contrast, as the rules can determine by the StudyDescription containing the word 'contrast'.

FIG. 1 is a flow chart showing how the rules are used to create the two Sets of Images shown in FIG. 2. As shown in FIG. 1, a primary Study 1105 which can be manually selected by a user. In step (i) 1120, based on Study Selection Rules 1115 which interrogate parameters in the primary Study 1105 such as DICOM Parameters and Abstract Tags of both the primary Study 1105 and the candidate studies 1110, the Study Selection Rules 1115 can identify additional candidate studies 1110. The second set of studies 1125 which includes the candidate studies 1110 and the primary Study 1105 are available to be loaded into Viewports 1160. In step (ii) 1140, the Protocol Selection Rules 1135 select a Display Protocol 1145 from the Available Display Protocols 1130 based on DICOM Parameters and Abstract Tags present in the second studies 1125. In step (iii) 1155, Image Set Rules 1150 are used to define a plurality of Image Sets 1165 from the second studies 1125. The one or more Viewports 1160 are defined in the Display Protocol 1145. In step (iv) 1175, Viewport Assignment Rules 1170 assign one or more Image Sets 1165 to one or more Viewports 1160. In step (v) 1185, Style Rules 1180 define a rendering style and rendering parameters. In an embodiment of the invention steps (i) through (v) are performed by a server processor running a render server program with an interface shown in FIG. 3 in which the rules (Study Selection Rules 1115, Protocol Selection Rules 1135, Image Set Rules 1150, Viewport Assignment Rules 1170, and the one or more Style Rules 1180) are used to automatically select and display the Image Sets 1165 in the Viewports 1160.

A render server program is described in U.S. application Ser. No. 13/831,967, entitled "Multi-User Mult-GPU Render Server Apparatus and Methods", inventors M. Westerhoff et al., which was filed Mar. 15, 2013, is herein expressly incorporated by reference in its entirety. A rule based render server program is described in U.S. application Ser. No. 13/831,982, entitled "Method and System for Transferring Data to Improve Responsiveness when Sending Large Data Sets", inventors D Stalling et al., which was filed Mar. 15, 2013 and issued Nov. 29, 2016 as U.S. Pat. No. 9,509,802, is herein incorporated by reference in its entirety.

Study Selection Rules 1115

In an embodiment of the present invention, based on the Study that the user selects for display (primary Study 1105), the system can first apply user defined rules to determine additional studies to be displayed together with the primary Study 1105. Such additional studies can be prior examinations that are relevant for the diagnosis of the current Study, or additional current studies. For example, a PET examination will often be looked at together with a CT examination acquired at the same time. The set of rules are constructed as follows:

Each rule consists of a matching criterion for the primary Study 1105 (primary condition), as well as matching criteria for additional studies (secondary condition). The matching criterion is an expression consisting of operators that allow evaluating the parameters of the Study and comparing them to defined values. The parameters of the Study are any parameters defined by the DICOM standard, such as Study Description, Study Date, Modality, Patient Age, as well as any other parameters that can be derived from the DICOM parameters or from the Study itself, such as number of images, or number of image series. The operators are numeric or string based operators, such as equals, greater than, less than, contains, etc. Expressions can be combined using Boolean operators such as AND, OR, NOT. Operators can also contain more complex expressions, including user defined functions defined in an appropriate programming language, such as JavaScript or VisualBasic.

Once a primary Study 1105 has been selected for display, the primary condition of each rule is evaluated. Those rules that match, i.e., evaluate to "true" for the given primary Study 1105, will then be applied to all other studies that are available for the same patient. Those other studies for which the secondary condition matches will be added to the list of studies to be displayed.

The following rule illustrates the concept. This rule will automatically load prior Chest X-Rays or prior Chest CT if the primary Study 1105 is a Chest X-RAY.

Study Selection Rule 1:
IF (Primary.Dicom.BodyPartExamined="CHEST" and Primary.Dicom.Modality="CR")
THEN SELECT other studies for loading WHERE (Other.Dicom. BodyPartExamined="CHEST" and (Other.Dicom.Modality="CR" or Other.Dicom.Modality="CT"))

The rule is expressed in pseudo-code with the primary condition specified in the IF-clause and the secondary condition expressed in the SELECT-clause.

Study Selection Rules: Normalization of DICOM Parameters

In an embodiment of the present invention, the rules can normalize DICOM parameters. As described above, a Study Selection Rule can contain arbitrary DICOM parameters. The DICOM standard specifies if a particular parameter is defined on a patient, Study, series, or image level. For example, a Study-level parameter should have the same value in all images of a Study, while a series-level parameter should have the same value in all images of a series. There are two problems related to assuming that this statement is always the case. Firstly, although a Study-level tag should have the same value for all images of a Study this is not always true. Secondly, some parameters are defined on a series- or image-level (e.g. modality is a series-level parameter) and therefore can be unavailable. In both cases it can be unclear what value is to be used when evaluating the rule. The invention described here provides different solutions to this problem.

In an embodiment of the present invention, a first approach is to choose a reference image and to read the value of a particular DICOM parameter from the reference image. The reference image can be: (i) the image that was inserted into the system first, (ii) the image with the oldest image content date, (iii) the image that was inserted into the system last, or (iv) the image with the earliest image content date. The choice of which image is to be chosen as the reference image can be configured for each parameter separately.

In an embodiment of the present invention, a second approach is to only allow original images to be chosen as the reference image. Non-viewable DICOM objects like structured reports, key objects, or presentation states are disregarded, as well as derived images such as secondary capture images or reformatted images.

In an embodiment of the present invention, a third approach is to provide a list of all distinct values that a particular DICOM parameter has in the images of a Study. In a Study Selection Rule one can then check if that list contains a particular value. The example above can then read as follows:
Study Selection Rule 2:
IF (Primary.Dicom.BodyPartExamined="CHEST" and Primary.DicomList.Modality contains "CR") THEN SELECT other studies for loading WHERE (Other.Dicom.BodyPartExamined="CHEST" and (Other.DicomList.Modality contains "CR" or Other.DicomList.Modality contains "CT"))
Study Selection Rules: Abstract Tags In an embodiment of the present invention, the Study Selection Rules 1115 contain other derived parameters such as Abstract Tags that characterize a Study in addition to or instead of DICOM parameters. Abstract tags that are useful within Study Selection Rules 1115 include the following:
(i) RelativeStudyAge indicates relative age of Study in days compared to primary Study 1105.
(ii) PriorIndex indicates an index that enumerates all other studies from youngest to oldest.
(iii) NumImages indicates number of images in Study.
(iv) NumSeries indicated number of image series in Study.
(v) Num3DVolumes indicates number of 3D volumes in Study.
(vi) Num4DSequences indicates number of 4D sequences in Study (e.g. Cardiac CT).
(vii) HasReport indicates a flag that indicates if a report is available for a Study.
(viii) HasThinSliceVolumes indicates whether the study has at least one set of images that form a true 3D volume, i.e. a sufficiently large number of equidistant slices (the exact number can be user configurable, e.g. 30 would be a common choice) and a sufficiently small spacing between two consecutive slices to guarantee an isotropic (or close to isotropic) (again, this parameter can be user defined, values between 1 mm and 3 mm are common thresholds for CT and MR examinations).

For example, a rule that applies to a Mammogram Study and that selects at maximum three prior Mammogram studies no older than five years can read as follows:
Study Selection Rule 3:
IF (Primary.Dicom.Modality="MG" THEN SELECT other studies for loading WHERE (Other.Dicom.Modality="MG" and Other.Abstract.PriorIndex<=3 and Other.Abstract.RelativeStudyAge<5*365)
Protocol Selection Rules 1135

In an embodiment of the present invention, once the studies to be displayed are determined as described above, a suitable display protocol can be selected. This is done using matching rules. Each matching rule consists of conditions that are applied to the primary and other studies to be loaded. Like in Study Selection Rules 1115, protocol selection rules may contain DICOM parameters (either taken from a reference image or provided as a list of distinct values gathered from all images of a study), as well as abstract tags and user-defined functions. Each matching rule has a score and an associated display protocol.

In an embodiment of the present invention, all matching rules are evaluated and the display protocol of the matching rule that evaluates to true can be selected. If multiple matching rules evaluate to true, the one with the highest score can be selected.

The following example rule illustrates a matching rule that can apply for PET/CT studies of the abdomen to select a protocol named "StandardPetCTProtocol1" with a score of 10.
Protocol Selection Rule 1:
IF (Primary.Dicom.BodyPartExamined="ABDOMEN" and Primary.Dicom.Modality="CT" and Exists(Other1) and Other1.Dicom.Modality="PET") THEN SELECT "StandardPetCTProtocol1" with score=10

In an embodiment of the present invention, the rule is expressed in pseudo-code with the matching condition specified in the IF-clause and the chosen protocol specified by the SELECT.
Image Set Rules 1150

In an embodiment of the present invention, once a display protocol is selected, further rules defined within the protocol are evaluated. The next step comprises creation of so-called image sets. An image set consists of images that are logically grouped together. Usually, an image set is represented by a single preview icon in the application. It is an image set that is loaded into a viewer or tiled viewer. Note that DICOM series also represent a logical grouping of images. However, often DICOM series are not well suited for hanging of images and viewing. For example, in Mammography a single DICOM series may contain images of both left and right breast, in MRI it may contain both T1 and T2 images, or in CT it may contain both a localizer image (topogram) and a 3D image stack. In all these cases the DICOM series can be split into different logical image sets. On the other hand, multiple DICOM series may represent the phases of a single 4D cardiac data set. In this case all those series can be joined into a single logical image set.

Thus the creation of image sets based on rules is a key component of the rule-based display system, specifically for the more advanced rendering techniques. For example, the rules-based display system is used to create image sets that are very similar to the rules described above in Study Selection Rules 1115 and Protocol Selection Rules 1135 sections. A rule is a Boolean expression that can contain DICOM parameters, abstract tags, or used-defined functions that are based on the DICOM parameters, abstract tags, or used-defined functions. Image set rules however, are applied to all images of a study that was selected for loading (and not to the study itself). Image-level parameters thus represent no problem and do not need to be normalized or otherwise treated specially. All images that match an image-set rule are grouped into a respective image set.

In an embodiment of the present invention, the following rule (expressed in pseudo-code) collects all images of a current CT study:

Image Set Rule 1:
   IF (Dicom.Modality="CT" and Abstract.PriorIndex=0)
   THEN CREATE image set with ID 1

In an embodiment of the present invention, the resulting image sets can be assigned IDs or names that allow for referencing the image sets later in layout and display set rules. In the above example an image set with ID 1 was defined. If no image matches an image set rule, no such corresponding image set will be created.

Image Set Rules: Sorting

In an embodiment of the present invention, the order of images within an image set is an important aspect. It determines how images are shown when the user browses through the image set or how images are distributed into the tiles of a tiled viewer. In one embodiment of the present invention, in order to specify image sorting, the image set rules can contain an ordered list of sorting criteria. All images that are matched by a rule are sorted according to those criteria.

For example, the following rule collects all images of a current CT study and sorts them according to DICOM series number at first and DICOM instance/image number at second.

Image Set Rule 2:
   IF (Dicom.Modality="CT" and Abstract.PriorIndex=0)
   THEN CREATE image set with ID 1
     SORTED BY Dicom.SeriesNumber ORDER:=ascending
     SORTED BY Dicom. InstanceNumber ORDER:=ascending Image Set Rules: Splitting In an embodiment of the present invention, sorting criteria can be extended by a split flag. With the split flag it is possible to create multiple image sets from a single image set rule. When the value of a sorting criterion with split flag set to true changes, sub-sequent images are automatically inserted into a new image set. The resulting image sets are automatically enumerated by a sub-level ID.

For example, the following rule essentially creates image sets that correspond to DICOM series, because all images with different series number will be split into different sets:

Image Set Rule 3:
   IF (Dicom.Modality="CT" and Abstract.PriorIndex=0)
   THEN CREATE image set with ID 1.x
     SORTED BY Dicom.SeriesNumber ORDER:=ascending SPLIT:=true
     SORTED BY Dicom. InstanceNumber ORDER:=ascending SPLIT:=false In applications where a CT has been measured, it can happen that a study contains both a soft-kernel series and a hard kernel series and both series have the same series number. In order to separate the images into different image sets the above rule can be extended by the following:

Image Set Rule 4:
   IF (Dicom.Modality="CT" and Abstract.PriorIndex=0)
   THEN CREATE image set with ID 1.x
     SORTED BY Condition.CTSoftTisseKernel SPLIT:=true
     SORTED BY Dicom.SeriesNumber ORDER:=ascending SPLIT:=true
     SORTED BY Dicom. InstanceNumber ORDER:=ascending SPLIT:=false Here, Condition.CTSoftTissueKernel denotes a user-defined Boolean condition that tests whether an image has a CT soft-tissue kernel. The actual implementation of this condition can for example evaluate the manufacturer (which is encoded in a DICOM parameter). Depending on its value the rule can evaluate further parameters to find out if an image was reconstructed using a soft-tissue kernel or not. Since this Boolean condition was used as a sorting criterion with the split flag set to true, all non-soft-kernel images can be put into an image set with ID 1.1 and all soft-kernel images can be put into an image set with ID 1.2 (unless the image set is further split and IDs like 1.3 or 1.4 are created).

Image Set Rules: More Abstract Tags

In an embodiment of the present invention, additional abstract tags are used in image set rules. One example is a tag that identifies whether an image has already been put into an image set. In principle, a single image can be put into multiple image sets, but sometimes this should be avoided. This can be achieved by evaluating image set rules in a pre-defined order and introducing an abstract tag AlreadyReferenced.

For example, in CT study that has a localizer image and a 3D image stack both stored in one DICOM series, one may want to create an image set, one for the localizer and one for the 3D image stack. Accordingly, the image set rules are defined as follows:

Image Set Rule 5 (Localizer):
   IF (Dicom.Modality="CT" and Condition.IsLocalizer=true)
   THEN CREATE image set with ID 1
     SORTED BY Dicom.SeriesNumber ORDER:=ascending SPLIT:=true
     SORTED BY Dicom. InstanceNumber ORDER:=ascending SPLIT:=false Image Set Rule 6 (Images):
   IF (Dicom.Modality="CT" and Abstract.AlreadyReferenced=false)
   THEN CREATE image set with ID 2
     SORTED BY Dicom.SeriesNumber ORDER:=ascending SPLIT:=true
     SORTED BY Dicom. InstanceNumber ORDER:=ascending SPLIT:=false Here Condition.IsLocalizer is a user-defined condition that returns true if an image is a localizer image, and false otherwise. In an embodiment of the present invention, Rule 1 is applied first. Therefore the localizer image is put into a separate image set with ID 1. Next rule 2 is applied. This rule can match for all CT images including the localizer image. However, because AlreadyReferenced=false is specified, the localizer image is skipped and not placed into image set 2.

In an embodiment of the present invention, the creation of the image sets based on rules is a key component of the efficient rules based display, specifically for the more advanced rendering techniques. For example rules can be used to identify sets of 2D images that together form a 3D volume.

Viewer Assignment Rules

In another embodiment of the present invention, a display protocol defines multiple viewers, each with one or more tiles, i.e., viewports. To each viewer one or more image sets can be assigned based on Viewer Assignment Rules that are similar to the protocol section rules described herein. Viewer Assignment Rules are defined in the display protocol. The rules determine which image set shall be initially shown in a viewer. In case multiple image sets are assigned to a viewer, the one with the highest score is chosen. Afterwards users may cycle quickly through the remaining image sets using dedicated tools (Previous/Next Image Set), or pick another image set from a special image set menu.

Like the other rule types Viewer Assignment Rules contain Boolean expressions of DICOM parameters, abstract tags, or user-defined conditions based on DICOM parameters, or abstract tags. In many cases it is sufficient to specify the image sets to be assigned to a viewer by their image set ID instead of evaluating the underlying DICOM parameters and abstract tags again. Therefore, the image set ID is simply set as a separate abstract tag. In the following example the two rules load image sets with the IDs 1 and 2 into a viewer, but assign ID 1 a higher score so that this image set is initially visible (provided such an image set exists):

Viewer Assignment Rule 1:
 IF (EXISTS ImageSet[1])
 THEN Viewport[0].AddImageSet(ID=1, score=10)
Viewer Assignment Rule 2:
 IF (EXISTS ImageSet[2])
 THEN
 Viewport[0].AddImageSet(ID=2, score=5)

In an embodiment of the present invention, viewer assignment rules are applied to image sets. Thus there is a possible conflict regarding ambiguous image-level and series-level tags. This conflict is resolved in the same way as described herein in the Normalization of DICOM Parameters section. This means that values of DICOM parameters, but also abstract tags, are automatically taken from some reference image. Alternatively, for all DICOM parameters a list of distinct values occurring in all images of the image set can be used in an assignment rule.

Style Rules

In one embodiment of the present invention, there is a final set of rules that specify the rendering style and other rendering parameters to be used when showing a particular image set. For example, for a CT Angiography study, often a volume rendering style display (VRT) is desired, whereas for a study looking for lung nodules a maximum intensity projection (MIP) of 20 mm slabs may be desired. Style rules, that can be user specific, allow driving that automatically. The rules can use the same parameters as discussed above, as well as the existence or absence of certain image sets.

In one embodiment of the present invention, the system uses a global, ordered list of style rules that is evaluated independently for each viewer and each image set loaded into a viewer. An abstract tag DisplaySetID is provided that allows formulating style rules for a specific viewer or group of viewers.

Parameters driven by Style Rules include the following:
 i) Rendering style (can be 2D, oblique, curved, MIP slab, 3D MIP, VRT, shaded VRT, etc.);
 ii) Image alignment (left, right, top, bottom, centered);
 iii) Inverse display (black on white versus white on black);
 iv) Colormap or transfer function;
 v) Window/level (data window);
 vi) Slice thickness;
 vii) Zoom factor;
 viii) Camera position and orientation; and
 ix) Labels/OverlayDisplay of labels, annotations and other overlay elements.

The following is an example of a style rule that activates inverse 3D MIP rendering in all viewers with a DisplaySetID between 101 and 104, provided a PET data set is loaded into those viewers (modality PT, i.e., positron emission tomography). Also, an automatic window/level setting is used that is computed from the histogram of the image set (the 2% lowest values are all mapped to white, and the 2% highest values are all mapped to black):

Style Rule 1:
 IF (Abstract.DisplaySetID>100 and
 Abstract.DisplaySetID<105 and
 Dicom.Modality="PT")
 THEN SET
 RenderingStyle:="3D MIP"
 Inverse:=true
 DataWindow:="2% 98%"

The following is another example of a different style rule that always causes the image set with image set ID 200 to be displayed in MPR mode using 20 mm thick slices, with a window/level as specified in the DICOM parameters, and with a zoom factor so that the whole viewer window is filled out. The rule is:

Style Rule 2:
 IF (Abstract.ImageSetID=200)
 THEN SET
 RenderingStyle:="MPR"
 SliceThickness:="20"
 DataWindow:="DICOM1"
 ZoomFactor:="FitToWindow"

Summary of Rule Types

Table I summarizes all types of rules that are applied in the rule-base display system:

TABLE I

| Rule Type | Applies to | Normalized Parameters | Defined where |
|---|---|---|---|
| Study Selection Rule | Studies | yes | globally |
| Protocol Selection Rule | Studies | yes | globally |
| Image Set Rule | Images | not required | protocol |
| Viewer Assignment Rule | Image Sets | yes | globally, protocol |
| Style Rule | Image Sets | yes | globally, protocol |

Described above are methods and systems for implementing a rule derived basis to display image sets. The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.
Example Shown in FIG. 2

An example of how these aspects can be combined is shown in FIG. 2. In the example the user has selected a CT examination of the abdomen. The following rules have been used to determine that a recent X-Ray of the chest is relevant and shall be displayed as well:
IF (Primary.Dicom.BodyPartExamined="ABDOMEN" and Primary.Dicom.Modality="CT")
THEN SELECT other studies for loading WHERE (Other.Dicom. BodyPartExamined="ABDOMEN" OR Other.Dicom. BodyPartExamined="CHEST") and (Other.Dicom.Modality="CR" or Other.Dicom.Modality="CT") AND Other.RelativeStudyAge<"90 days"

From this rule, a hanging protocol can be selected. In the example the protocol selection rules determine that the CT study is a thin slice CT study (i.e. that it has image series that form a 3D volume with sufficient resolution in all directions to display volume rendering or non-axial slices in a meaningful way). Furthermore the example rule determines that this is a study with enhanced vasculature, by looking for the key words "contrast" or "angio" in the study description. The display protocol selection rule that applies here and select the protocol CTThinSliceVesselWithPrior can read
IF (Primary.Dicom.BodyPartExamined="ABDOMEN" and Primary.Dicom.Modality="CT" and Primary.Abstract.HasThinSliceVolumes and (Primary.Dicom.StudyDescription containsAnyOf "contrast, angio" and exists Other1 THEN SELECT "CTThinSliceVesselWithPrior" with score=10
From this image sets are generated using Image Set Rules:
IF (Dicom.Modality="CT" and Abstract.PriorIndex=0 and
Condition.IsPartOfThinSliceVolume and Condition.CTSoftTisseKernel)
THEN CREATE image set with ID 1.x
SORTED BY Abstract.NumberOfSlicesInVolume ORDER:=descending SPLIT:=true
SORTED BY Dicom.SeriesNumber ORDER:=ascending SPLIT:=true
SORTED BY Dicom.Abstract.VolumeIndex ORDER:=ascending SPLIT:=true
SORTED BY Dicom.Abstract.SlicePosition ORDER:=ascending SPLIT:=false This rule will actually form sets from images that contain images that are part of a ThinSliceVolume and that have been reconstructed with a "soft tissue" kernel. Given the protocol selection rule has specifically matched for just CT studies, the conditions Dicom.Modality="CT" and Abstract.PriorIndex=0 are actually redundant, but could be useful if a different selection rule was used.

The images will first be sorted by the size of the volume of which they are part (Abstract.NumberOfSlicesInVolume), then by DICOM series. The split parameter in this case will ensure that an image set contains images from on series only. A DICOM series can sometimes contain multiple non-consecutive volumes. The abstract tag VolumeIndex will then indicate for each image, which of those volumes it is part of. If a series contains only one volume, then this will be "1" for all images in the series. The split=true in this part of the rule would result in a separate image set for each of those volumes. Finally, within each volume, the images are ordered by slice position, but not split. This way we end up with one image set for each soft kernel thin slice volume, the largest volume being the first image set (ID 1.1). This ID will be used further in subsequent rules.

The rule to form an image set from any CR prior study in this example is much simpler:
IF (Dicom.Modality="CR" and Abstract.PriorIndex=1)
THEN CREATE image set with ID 10
SORTED BY Dicom.SeriesNumber ORDER:=ascending SPLIT:=false
SORTED BY Dicom. InstanceNumber ORDER:=ascending SPLIT:=false This creates one image set with ID=10 containing all images for the first prior study, if that is a CR.

In practice, additional rules, such as Image Set Rule 5 and 6 (see above) will be used to collect the remaining images of the primary Study 1105. The remaining images are not shown in the layout depicted in the example FIG. 2.

The Display Protocol 1145 contains multiple layouts. The one shown in FIG. 2 is defined as follows:

```
DEFINE Layout {
  ID="Layout5";
  NAME="+PlainFilm"
  Viewports {
    { ID=50, Geometry="(0,0)-(0.25,0.5)"},
    { ID=51, Geometry="(0.25,0)-(0.5,0.5)"},
    { ID=52, Geometry="(0,0.5)-(0.25,1)"},
    { ID=53, Geometry="(0.25,0.5)-(0. 5,0.5)"},
    { ID=54, Geometry="(0.5,0)-(1,1)", Style="2D"}
  }
}
```

In this example the geometry is defined in a coordinate system having the origin in the upper left corner of the screen with the x axis pointing to the right and the y axis pointing down. Please note how parameters of the viewers can be set in the layout definition. Parameters can also be set or overridden in the assignment and style rules, as will be explained next.

In this example, viewer assignment and style rules are as follows:
IF ImageSetExists (1.1) and ImageSetExists(10) THEN
SHOW_LAYOUT Layout5 WITH
Viewport[0].AddImageSet(1.1)
Viewport [0].Style="VRT(diffuse)"
Viewport [0].Colormap="CTAngioSoftTissue"
Viewport [1,2,3].AddImageSet(1.1)
Viewport [1,2,3].Style="MPR"
Viewport [1,2,3].DataWindow="DICOM1"
Viewport [1].oriantation="axial"
Viewport [2].oriantation="sagittal"
Viewport [3].oriantation="coronal"
Viewport [4].AddImageSet(10)
IF (ImageSet[10].Dicom.Columns>1024) THEN
Viewport[4].Zoom="FitToWindow"
ELSE
Viewport[4].Zoom="1:1"

In this particular example, the rule to select the layout is rather simple: It is shown if the two image sets used exist. This is because the criteria to construct these images sets have been rather specific. As will be appreciated, the proposed system gives this type of flexibility.

ASPECTS OF THE INVENTION

Some aspects of this invention include methods of displaying one or more Sets of Images comprising the steps of:
a. selecting a primary Study;
b. selecting one or more Study Selection Parameters based on the primary Study;

c. selecting one or more Study Selection Rules based on the one or more Study Selection Parameters;
d. selecting one or more Sets of Images from a plurality of images based on the one or more Study Selection Rules;
e. selecting one or more Display Protocol Selection Parameters based on the one or more Sets of Images selected;
f. selecting one or more Display Protocol Selection Rules based on the one or more Display Protocol Selection Parameters;
g. selecting one or more Display Parameters using the one or more Display Protocol Selection Rules; and
h. displaying the one or more Sets of Images according to the Display Parameters.

Additional aspects include methods one or more Display Parameter are selected from the group consisting of Image Set Selection Parameters and View and Viewport Selection Parameters.

Further aspects include methods where the one or more Display Parameters are selected from the group consisting of Image Set Selection Rules, View and Viewport Selection Rules, and Display Protocol Selection Rules.

Yet further aspects include methods where the step of identifying one or more Image Set Selection Rules is based on the one or more Image Set Selection Parameters.

Still further aspects include methods where the step of selecting one or more Viewpoint Selection Rules is based on one or more View and Viewport Selection Parameters.

Other aspects include methods where the step of displaying the one or more Sets of Images is based on one or more Display Protocol Selection Rules, one or more Image Set Selection Rules, and one or more View and Viewport Selection Rules.

Still other aspects include methods where one or more of the Study Selection Parameters are selected from the group consisting of DICOM parameters and Abstract Tags.

Other aspects include methods where one or more of the Display Protocol Selection Parameters are selected from the group consisting of DICOM parameters and Abstract Tags.

Additional aspects include methods where one or more of the Image Set Selection Parameters are selected from the group consisting of DICOM parameters and Abstract Tags.

Further aspects include methods where one or more of the View and Viewport Selection Parameters are selected from the group consisting of DICOM parameters and Abstract Tags.

More aspects include methods where one or more Study Selection Parameters are derived from a single reference image.

Still more aspects include methods where one or more Study Selection Parameters are derived from a single reference image DICOM Parameters.

Yet other aspects include methods where one or more Display Protocol Selection Parameters are derived using a list of all values of a DICOM parameter occurring in any of the one or more Sets of Images.

Alternative aspects include methods where the one or more View and Viewport Selection Rules contain protocols for one or more Viewports displaying images as 2D.

Other alternative aspects include methods where the one or more View and Viewport Selection Rules contain protocols for one or more Viewports displaying images in a 3D rendering mode.

Further alternative aspects include methods where one or more Study Selection Parameters include one or more Abstract Tags selected from the group consisting of RelativeStudyAge, PriorIndex. NumImages, NumSeries, Num3DVolumes, Num4DSequences and HasReport.

In other aspects, this invention includes methods where one or more View and Viewport Selection Rules include one or more Abstract Tags selected from the group consisting of Image Sets to be displayed, Rendering Style, Additional image sets for image fusion, Image Alignment, Colormap/Transfer Function, Slice Thickness, Zoom Factor, Camera position, Camera orientation and Labels/Overlay elements.

In still other aspects, this invention includes methods further comprising the steps of:
  receiving one or more Sets of Images based on the Study Selection Rules;
  selecting one or more Image Set Selection Parameters;
  selecting one or more Image Set Selection Rules based on the one or more Image Set Selection Parameters; and
  displaying the one or more Sets of Images based on the Display Protocol Selection Rules and the Image Set Selection Rules.

In another aspect, this invention includes methods of displaying one or more Sets of Images comprising the steps of:
  selecting one or more Study Selection Parameters;
  selecting or more Study Selection Rules based on the one or more Study Selection Parameters;
  receiving one or more Sets of Images based on the Study Selection Rules;
  selecting one or more Display Protocol Selection Parameters based on the one or more Sets of Images selected;
  selecting one or more Display Protocol Selection Rules based on the one or more Display Protocol Selection Parameters; and
  displaying the one or more Sets of Images based on the Display Protocol Selection Rules.

Another aspect of this invention includes methods of displaying images comprising the steps of:
  a. selecting one or more Study Selection Parameters;
  b. selecting Study Selection Rules based on the one or more Study Selection Parameters;
  c. receiving one or more images based on the Study Selection Rules;
  d. selecting one or more Display Protocol Selection Parameters based on the one or more images selected;
  e. selecting Display Protocol Selection Rules based on the one or more Display Protocol Selection Parameters;
  f. selecting one or more Image Set Selection Parameters;
  g. selecting Image Set Selection Rules based on the one or more Image Set Selection Parameters;
  h. selecting one or more View and Viewport Selection Parameters;
  i. selecting View and Viewport Selection Rules based on the one or more View and Viewport Selection Parameters; and
  j. displaying the one or more images based on the Display Protocol Selection Rules, the Image Set Selection Rules and the View and Viewport Selection Rules.

Other aspects of the invention include methods where the Study Selection Rule is:
  IF (Primary.Dicom.BodyPartExamined="CHEST" and Primary.Dicom.Modality="CR")
  THEN SELECT other studies for loading WHERE (Other.Dicom.BodyPartExamined="CHEST" and (Other.Dicom.Modality="CR" or Other.Dicom.Modality="CT")).

In another aspect, this invention includes methods where the Study Selection Rule is:

IF (Primary.Dicom.BodyPartExamined="CHEST" and
   Primary.DicomList.Modality contains "CR") THEN
   SELECT other studies for loading WHERE
   (Other.Dicom.BodyPartExamined="CHEST" and (Other.DicomList.Modality contains "CR" or Other.DicomList.Modality contains "CT")).

In other aspects, this invention includes methods where the Study Selection Rule is:
IF (Primary.Dicom.Modality="MG" THEN SELECT
   other studies for loading WHERE
   (Other.Dicom.Modality="MG" and Other.Abstract.PriorIndex<=3 and
   Other.Abstract.RelativeStudyAge<5*365).

In yet another aspect, this invention includes methods where the Protocol Selection Rule is:
IF (Primary.Dicom.BodyPartExamined="ABDOMEN"
   and Primary.Dicom.Modality="CT" and Exists
   (Other1) and Other1.Dicom.Modality="PET") THEN
   SELECT "StandardPetCTProtocol1" with score=10.

In aspects of the invention, methods include an Image Set Rule:
IF (Dicom.Modality="CT" and Abstract.PriorIndex=0)
THEN CREATE image set with ID 1.

Additionally, other aspects include methods where the Image Set Rule is:
IF (Dicom.Modality="CT" and Abstract.PriorIndex=0)
THEN CREATE image set with ID 1
   SORTED BY Dicom.SeriesNumber ORDER:=ascending
   SORTED BY Dicom. InstanceNumber ORDER:=ascending.

Still other aspects include methods where the Image Set Rule is:
IF (Dicom.Modality="CT" and Abstract.PriorIndex=0)
THEN CREATE image set with ID 1.x
   SORTED BY Dicom.SeriesNumber ORDER:=ascending SPLIT:=true
   SORTED BY Dicom. InstanceNumber ORDER:=ascending SPLIT:=false.

Moreover, other aspects include methods where the Image Set Rule is:
IF (Dicom.Modality="CT" and Abstract.PriorIndex=0)
THEN CREATE image set with ID 1.x
   SORTED BY Condition.CTSoftTisseKernel SPLIT:=true
   SORTED BY Dicom.SeriesNumber ORDER:=ascending SPLIT:=true
   SORTED BY Dicom. InstanceNumber ORDER:=ascending SPLIT:=false.

Yet other aspects include methods where the Image Set Rule (Localizer) is:
IF (Dicom.Modality="CT" and
   Condition.IsLocalizer=true)
THEN CREATE image set with ID 1
   SORTED BY Dicom.SeriesNumber ORDER:=ascending SPLIT:=true
   SORTED BY Dicom. InstanceNumber ORDER:=ascending SPLIT:=false.

Other aspects of the methods of this invention include an Image Set Rule (Images):
IF (Dicom.Modality="CT" and
   Abstract.AlreadyReferenced=false)
THEN CREATE image set with ID 2
   SORTED BY Dicom.SeriesNumber ORDER:=ascending SPLIT:=true
   SORTED BY Dicom. InstanceNumber ORDER:=ascending SPLIT:=false.

Yet other aspects of the methods of this invention include using Image Set Rule (Images):
IF (Dicom.Modality="CT" and
   Abstract.AlreadyReferenced=false)
THEN CREATE image set with ID 2
   SORTED BY Dicom.SeriesNumber ORDER:=ascending SPLIT:=true
   SORTED BY Dicom. InstanceNumber ORDER:=ascending SPLIT:=false.

Additionally, other aspects include methods where the Display Parameters include Viewer Assignment Rule:
IF (Abstract.ImageSetID=1)
THEN SELECT image set with score=10.

Yet further aspects include methods where the Display Parameters include a Viewer Assignment Rule:
IF (Abstract.ImageSetID=2)
THEN SELECT image set with score=5.

Additional aspects include methods further comprising a Viewer Assignment Rule:
IF (Abstract.ImageSetID=2)
THEN SELECT image set with score=5.

In other aspects of this invention, methods include one or more Study Selection Rules comprising one or more Abstract Tags selected from the group consisting of:
(i) RelativeStudyAge indicates relative age of Study in days compared to primary Study 1105.
(ii) PriorIndex indicates an index that enumerates all other studies from youngest to oldest.
(iii) NumImages indicates number of images in Study.
(iv) NumSeries indicated number of image series in Study.
(v) Num3DVolumes indicates number of 3D volumes in Study.
(vi) Num4DSequences indicates number of 4D sequences in Study (e.g. Cardiac CT).
(vii) HasReport indicates a flag that indicates if a report is available for a Study.
(viii) IsThinSliceVolume.

Aspects of methods also include a step of displaying including use of an Abstract Tag DisplaySetID.

Other aspects of methods include Abstract Tag DisplaySetID having a Style Rule selected from the group consisting of:
i) Rendering style (can be 2D, oblique, curved, MIP slab, 3D MIP, VRT, shaded VRT, etc.);
ii) Image alignment (left, right, top, bottom, centered);
iii) Inverse display (black on white versus white on black);
iv) Colormap or transfer function;
v) Window/level (data window);
vi) Slice thickness;
vii) Zoom factor;
viii) Camera position and orientation; and
ix) Labels/OverlayDisplay of labels, annotations and other overlay elements.

Still other methods include steps where the Style Rule is:
IF (Abstract.DisplaySetID>100 and
   Abstract.DisplaySetID<105 and
   Dicom.Modality="PT")
THEN SET
   RenderingStyle:="3D MIP"
   Inverse:=true
   DataWindow:="2% 98%".

Other aspects of methods include use of a Style Rule:
IF (Abstract.ImageSetID=200)
THEN SET
RenderingStyle:="MPR"
SliceThickness:="20"
DataWindow:="DICOM1"
ZoomFactor:="FitToWindow", Another aspect of the present invention is a method of displaying one or more Sets of Images comprising the steps of:
selecting one or more Study Selection Parameters;
identifying one or more Study Selection Rules based on the one or more Study Selection Parameters;
selecting one or more Sets of Images from a plurality of images based on the one or more Study Selection Rules;
selecting one or more Display Protocol Selection Parameters based on the one or more Sets of Images selected;
identifying one or more Display Protocol Selection Rules based on the one or more Display Protocol Selection Parameters;
using the one or more Display Protocol Selection Rules to select one or more Display Parameters; and
displaying the one or more Sets of Images according to the Display Parameters.

Still other aspects of methods of displaying one or more Sets of Images comprising the steps of:
selecting one or more Study Selection Parameters;
selecting Study Selection Rules based on the one or more Study Selection Parameters;
selecting one or more Sets of Images based on the Study Selection Rules;
selecting one or more Display Protocol Selection Parameters based on the one or more Sets of Images selected;
selecting Display Protocol Selection Rules based on the one or more Display Protocol Selection Parameters;
selecting one or more Image Set Selection Parameters;
selecting Image Set Selection Rules based on the one or more Image Set Selection Parameters;
selecting one or more View and Viewport Selection Parameters;
selecting View and Viewport Selection Rules based on the one or more View and Viewport Selection Parameters; and
displaying the one or more Sets of Images based on the Display Protocol Selection Rules, the Image Set Selection Rules and the View and Viewport Selection Rules.

In systems of this invention, aspects include system for displaying one or more Sets of Images comprising:
one or more digital data processors for carrying out the steps including:
selecting one or more Study Selection Parameters;
selecting one or more Study Selection Rules based on the one or more Study Selection Parameters;
receiving one or more Sets of Images based on the Study Selection Rules;
selecting one or more Display Protocol Selection Parameters based on the one or more Sets of Images selected;
selecting Display Protocol Selection Rules based on the one or more Display Protocol Selection Parameters;
selecting one or more Image Set Selection Parameters;
selecting one or more Image Set Selection Rules based on the one or more Image Set Selection Parameters;
selecting one or more View and Viewport Selection Parameters;
selecting View and Viewport Selection Rules based on the one or more View and Viewport Selection Parameters; and
graphics resources for displaying the one or more Sets of Images based on one or more of Display Protocol Selection Rules, Image Set Selection Rules, the View and Viewport Selection Rules, and Viewer Assignment Rules.

Additional system aspects include Sets of Images comprising:
one or more digital data processors for carrying out the steps according to any of the above described methods aspects;
and graphics resources for displaying the one or more Sets of Images.

In an embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In another embodiment of the invention, a method of displaying images comprises the steps of:
selecting one or more Study Selection Parameters;
identifying a Study Selection Rule based on the one or more Study Selection Parameters, where the Study Selection Rule is:
IF (Primary.Dicom.BodyPartExamined="CHEST" and Primary.Dicom.Modality="CR")
THEN SELECT other studies for loading WHERE (Other.Dicom. BodyPartExamined="CHEST" and (Other.Dicom.Modality="CR" or Other.Dicom.Modality="CT"));
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters; selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In an alternative embodiment of the invention, a method of displaying images comprises the steps of:

selecting one or more Study Selection Parameters;
identifying a Study Selection Rule based on the one or more Study Selection Parameters, where the Study Selection Rule is:
IF (Primary.Dicom.BodyPartExamined="CHEST" and Primary.DicomList.Modality contains "CR") THEN SELECT other studies for loading WHERE (Other.Dicom.BodyPartExamined="CHEST" and (Other.DicomList.Modality contains "CR" or Other.DicomList.Modality contains "CT"));
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In another alternative embodiment of the invention, a method of displaying images comprises the steps of:
selecting one or more Study Selection Parameters;
identifying a Study Selection Rule based on the one or more Study Selection Parameters, where the Study Selection Rule is:
IF (Primary.Dicom.Modality="MG" THEN SELECT other studies for loading WHERE (Other.Dicom.Modality="MG" and Other.Abstract.PriorIndex<=3 and Other.Abstract.RelativeStudyAge<5*365);
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In an embodiment of the invention, a method of displaying images comprises the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying a Display Protocol Selection Rule based on the one or more Display Protocol Selection Parameters, where the Display Protocol Selection Rule is:
IF (Primary.Dicom.BodyPartExamined="ABDOMEN" and Primary.Dicom.Modality="CT" and Exists (Other1) and Other1.Dicom.Modality="PET") THEN SELECT "StandardPetCTProtocol1" with score=10;
selecting one or more Image Set Selection Parameters;
identifying Image Set Selection Rules based on the one or more Image Set Selection Parameters; selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In a further embodiment of the invention, a method of displaying images comprises the steps of:
selecting one or more Study Selection Parameters;
identifying Study Selection Rules based on the one or more Study Selection Parameters; receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters, where the Image Set Selection Rule is:
IF (Dicom.Modality="CT" and Abstract.PriorIndex=0) THEN CREATE image set with ID 1;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In an additional embodiment of the invention, a method of displaying images comprises the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters, where the Image Set Selection Rule is:
IF (Dicom.Modality="CT" and Abstract.PriorIndex=0) THEN CREATE image set with ID 1
SORTED BY Dicom.SeriesNumber ORDER:=ascending
SORTED BY Dicom.InstanceNumber ORDER:=ascending;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In another embodiment of the invention, a method of displaying images comprises the steps of:
 selecting one or more Study Selection Parameters;
 identifying Study Selection Rules based on the one or more Study Selection Parameters; receiving one or more images based on the Study Selection Rules;
 selecting one or more Display Protocol Selection Parameters based on the one or more images selected;
 identifying Display Protocol Selection Rules based on the one or more Display Protocol Selection Parameters;
 selecting one or more Image Set Selection Parameters;
 identifying Image Set Selection Rules based on the one or more Image Set Selection Parameters, where the Image Set Selection Rule is:
 IF (Dicom.Modality="CT" and Abstract.PriorIndex=0)
 THEN CREATE image set with ID 1.x
  SORTED BY Dicom.SeriesNumber ORDER:=ascending SPLIT:=true
  SORTED BY Dicom. InstanceNumber ORDER:=ascending SPLIT:=false;
 selecting one or more View and Viewport Selection Parameters;
 identifying View and Viewport Selection Rules based on the one or more View and Viewport Selection Parameters; and
 displaying the one or more images based on the Display Protocol Selection Rules, the Image Set Selection Rules and the View and Viewport Selection Rules.

In another further embodiment of the invention, a method of displaying images comprises the steps of:
 selecting one or more Study Selection Parameters;
 identifying Study Selection Rules based on the one or more Study Selection Parameters;
 receiving one or more images based on the Study Selection Rules;
 selecting one or more Display Protocol Selection Parameters based on the one or more images selected;
 identifying Display Protocol Selection Rules based on the one or more Display Protocol Selection Parameters;
 selecting one or more Image Set Selection Parameters;
 identifying Image Set Selection Rules based on the one or more Image Set Selection Parameters,
 where the Image Set Selection Rule is:
 IF (Dicom.Modality="CT" and Abstract.PriorIndex=0)
 THEN CREATE image set with ID 1.x
  SORTED BY Condition.CTSoftTisseKernel SPLIT:=true
  SORTED BY Dicom.SeriesNumber ORDER:=ascending SPLIT:=true
  SORTED BY Dicom. InstanceNumber ORDER:=ascending SPLIT:=false;
 selecting one or more View and Viewport Selection Parameters;
 identifying View and Viewport Selection Rules based on the one or more View and Viewport Selection Parameters; and
 displaying the one or more images based on the Display Protocol Selection Rules, the Image Set Selection Rules and the View and Viewport Selection Rules.

In an embodiment of the invention, a method of displaying images comprising the steps of:
 selecting one or more Study Selection Parameters;
 identifying Study Selection Rules based on the one or more Study Selection Parameters;
 receiving one or more images based on the Study Selection Rules;
 selecting one or more Display Protocol Selection Parameters based on the one or more images selected;
 identifying Display Protocol Selection Rules based on the one or more Display Protocol Selection Parameters;
 selecting one or more Image Set Selection Parameters;
 identifying an Image Set Selection Rule based on the one or more Image Set Selection Parameters,
 where the Image Set Selection Rule (Localizer) is:
 IF (Dicom.Modality="CT" and Condition.IsLocalizer=true)
 THEN CREATE image set with ID 1
  SORTED BY Dicom.SeriesNumber ORDER:=ascending SPLIT:=true
  SORTED BY Dicom. InstanceNumber ORDER:=ascending SPLIT:=false;
 selecting one or more View and Viewport Selection Parameters;
 identifying View and Viewport Selection Rules based on the one or more View and Viewport Selection Parameters; and
 displaying the one or more images based on the Display Protocol Selection Rules, the Image Set Selection Rules and the View and Viewport Selection Rules.

In a further embodiment of the invention, a method of displaying images comprising the steps of:
 selecting one or more Study Selection Parameters;
 identifying Study Selection Rules based on the one or more Study Selection Parameters;
 receiving one or more images based on the Study Selection Rules;
 selecting one or more Display Protocol Selection Parameters based on the one or more images selected;
 identifying Display Protocol Selection Rules based on the one or more Display Protocol Selection Parameters;
 selecting one or more Image Set Selection Parameters;
 identifying an Image Set Selection Rule based on the one or more Image Set Selection Parameters,
 where the Image Set Selection Rule (Localizer) is:
 IF (Dicom.Modality="CT" and Condition.IsLocalizer=true)
 THEN CREATE image set with ID 1
  SORTED BY Dicom.SeriesNumber ORDER:=ascending SPLIT:=true
  SORTED BY Dicom. InstanceNumber ORDER:=ascending SPLIT:=false;
 selecting one or more View and Viewport Selection Parameters;
 identifying View and Viewport Selection Rules based on the one or more View and Viewport Selection Parameters; and
 displaying the one or more images based on the Display Protocol Selection Rules, the Image Set Selection Rules and the View and Viewport Selection Rules.

In a still further embodiment of the invention, a method of displaying images comprising the steps of:
 selecting one or more Study Selection Parameters;
 identifying Study Selection Rules based on the one or more Study Selection Parameters;
 receiving one or more images based on the Study Selection Rules;
 selecting one or more Display Protocol Selection Parameters based on the one or more images selected;
 identifying Display Protocol Selection Rules based on the one or more Display Protocol Selection Parameters;

selecting one or more Image Set Selection Parameters;
identifying an Image Set Selection Rule based on the one or more Image Set Selection Parameters,
where the Image Set Selection Rule (Localizer) is:
IF (Dicom.Modality="CT" and Abstract.AlreadyReferenced=false)
THEN CREATE image set with ID 2
SORTED BY Dicom.SeriesNumber ORDER:=ascending SPLIT:=true
SORTED BY Dicom. InstanceNumber ORDER:=ascending SPLIT:=false;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In a further embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying an Image Set Selection Rule based on the one or more Image Set Selection Parameters,
where the Image Set Selection Rule (Localizer) is:
IF (Dicom.Modality="CT" and Abstract.AlreadyReferenced=false)
THEN CREATE image set with ID 2
SORTED BY Dicom.SeriesNumber ORDER:=ascending SPLIT:=true
SORTED BY Dicom. InstanceNumber ORDER:=ascending SPLIT:=false;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In another embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected, where the one or more Display Protocol Selection Parameters include Viewer Assignment Rule:
IF (Abstract.ImageSetID=1)
THEN SELECT image set with score=10;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In an additional embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected, where the one or more Display Protocol Selection Parameters include Viewer Assignment Rule:
IF (Abstract.ImageSetID=1)
THEN SELECT image set with score=10;
identifying Display Protocol Selection Rules based on the one or more Display Protocol Selection Parameters;
selecting one or more Image Set Selection Parameters;
identifying Image Set Selection Rules based on the one or more Image Set Selection Parameters; selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In a further embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected, where the one or more Display Protocol Selection Parameters include Viewer Assignment Rule:
IF (Abstract.ImageSetID=2)
THEN SELECT image set with score=5;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In a still further embodiment of the invention, a method of displaying images comprising the steps of:
selecting one or more Study Selection Parameters;
identifying Study Selection Rules based on the one or more Study Selection Parameters; receiving one or more images based on the Study Selection Rules;
selecting one or more Display Protocol Selection Parameters based on the one or more images selected;

identifying Display Protocol Selection Rules based on the one or more Display Protocol Selection Parameters;
selecting one or more Image Set Selection Parameters;
identifying Image Set Selection Rules based on the one or more Image Set Selection Parameters; selecting one or more View and Viewport Selection Parameters;
identifying View and Viewport Selection Rules based on the one or more View and Viewport Selection Parameters;
displaying the one or more images based on the Display Protocol Selection Rules, the Image Set Selection Rules and the View and Viewport Selection Rules; and
selecting Viewer Assignment Rule:
IF (Abstract.ImageSetID=2)
THEN SELECT image set with score=5.

In an embodiment of the invention, a method of displaying images comprising the steps of:
selecting one or more Study Selection Parameters;
identifying Study Selection Rules based on the one or more Study Selection Parameters, where the one or more Study Selection Rules comprise one or more Abstract Tags selected from the group consisting of:
(i) RelativeStudyAge indicates relative age of Study in days compared to primary Study.
(ii) PriorIndex indicates an index that enumerates all other studies from youngest to oldest.
(iii) NumImages indicates number of images in Study.
(iv) NumSeries indicated number of image series in Study.
(v) Num3DVolumes indicates number of 3D volumes in Study.
(vi) Num4DSequences indicates number of 4D sequences in Study (e.g. Cardiac CT).
(vii) HasReport indicates a flag that indicates if a report is available for a Study;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters; selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules.

In another embodiment of the invention, a method of displaying images comprising the steps of:
selecting one or more Study Selection Parameters;
identifying Study Selection Rules based on the one or more Study Selection Parameters; receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters;
selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules, where the step of displaying includes an Abstract Tag DisplaySetID.

In another embodiment of the invention, a method of displaying images comprising the steps of:
selecting one or more Study Selection Parameters;
identifying Study Selection Rules based on the one or more Study Selection Parameters;
receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters; selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules, where the step of displaying includes an Abstract Tag DisplaySetID, where the Abstract Tag DisplaySetID has a Style Rule selected from the group consisting of:
i) Rendering style (can be 2D, oblique, curved, MIP slab, 3D MIP, VRT, shaded VRT, etc.);
ii) Image alignment (left, right, top, bottom, centered);
iii) Inverse display (black on white versus white on black);
iv) Colormap or transfer function;
v) Window/level (data window);
vi) Slice thickness;
vii) Zoom factor;
viii) Camera position and orientation; and
ix) Labels/OverlayDisplay of labels, annotations and other overlay elements.

In a further embodiment of the invention, a method of displaying images comprising the steps of:
selecting one or more Study Selection Parameters;
identifying Study Selection Rules based on the one or more Study Selection Parameters; receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters; selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules, where the step of displaying includes an Abstract Tag DisplaySetID, where the Abstract Tag DisplaySetID has a Style Rule selected from the group consisting of:

i) Rendering style (can be 2D, oblique, curved, MIP slab, 3D MIP, VRT, shaded VRT, etc.);
ii) Image alignment (left, right, top, bottom, centered);
iii) Inverse display (black on white versus white on black);
iv) Colormap or transfer function;
v) Window/level (data window);
vi) Slice thickness;
vii) Zoom factor;
viii) Camera position and orientation; and
ix) Labels/OverlayDisplay of labels, annotations and other overlay elements, where the Style Rule is:
IF (Abstract.DisplaySetID>100 and
Abstract.DisplaySetID<105 and
Dicom.Modality="PT")
THEN SET
RenderingStyle:="3D MIP"
Inverse:=true
DataWindow:="2% 98%".

In a still further embodiment of the invention, a method of displaying images comprising the steps of:
selecting one or more Study Selection Parameters;
identifying Study Selection Rules based on the one or more Study Selection Parameters; receiving one or more images based on the Study Selection Rules;
selecting one or more Display Protocol Selection Parameters based on the one or more images selected;
identifying Display Protocol Selection Rules based on the one or more Display Protocol Selection Parameters;
selecting one or more Image Set Selection Parameters;
identifying Image Set Selection Rules based on the one or more Image Set Selection Parameters; selecting one or more View and Viewport Selection Parameters;
identifying View and Viewport Selection Rules based on the one or more View and Viewport Selection Parameters; and
displaying the one or more images based on the Display Protocol Selection Rules, the Image Set Selection Rules and the View and Viewport Selection Rules, where the step of displaying includes an Abstract Tag DisplaySetID, where the Abstract Tag DisplaySetID has a Style Rule selected from the group consisting of:
i) Rendering style (can be 2D, oblique, curved, MIP slab, 3D MIP, VRT, shaded VRT, etc.);
ii) Image alignment (left, right, top, bottom, centered);
iii) Inverse display (black on white versus white on black);
iv) Colormap or transfer function;
v) Window/level (data window);
vi) Slice thickness;
vii) Zoom factor;
viii) Camera position and orientation; and
ix) Labels/OverlayDisplay of labels, annotations and other overlay elements, where the Style Rule is:
IF (Abstract.ImageSetID=200)
THEN SET
RenderingStyle:="MPR"
SliceThickness:="20"
DataWindow:="DICOM1"
ZoomFactor:="FitToWindow".

In an embodiment of the invention, a method of displaying one or more Sets of Images comprises the steps of:
selecting one or more Study Selection Parameters;
selecting or more Study Selection Rules based on the one or more Study Selection Parameters;
receiving one or more Sets of Images based on the Study Selection Rules;
selecting one or more Display Protocol Selection Parameters based on the one or more Sets of Images selected;
selecting one or more Display Protocol Selection Rules based on the one or more Display Protocol Selection Parameters; and
displaying the one or more Sets of Images based on the Display Protocol Selection Rules.

In a further embodiment of the invention, a method of displaying one or more Sets of Images comprises the steps of:
a. selecting a primary Study;
b. selecting one or more Study Selection Parameters based on the primary Study;
c. selecting one or more Study Selection Rules based on the one or more Study Selection Parameters;
d. selecting one or more Sets of Images from a plurality of images based on the one or more Study Selection Rules;
e. selecting one or more Display Protocol Selection Parameters based on the one or more Sets of Images selected;
f. selecting one or more Display Protocol Selection Rules based on the one or more Display Protocol Selection Parameters;
g. selecting one or more Display Parameters using the one or more Display Protocol Selection Rules, where the one or more Display Parameter are selected from the group consisting of Image Set Selection Parameters and View and Viewport Selection Parameters; and
h. displaying the one or more Sets of Images according to the Display Parameters.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one study from the plurality of Image Sets is a two dimensional image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one study from the plurality of Image Sets is a three dimensional (3D) image displayed with a 3D rendering style.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays an oblique cross section through a volumetric image set.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a maximum intensity projection of an image set.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a post processed rendering of an image set.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a thick slab image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a volume rendered image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where at least one of the one or more Viewports displays a three dimensional image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where one or more Study Selection Rules used DICOM parameters and Abstract Tags derived from a single reference image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the primary Study selected is a single reference image.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the primary Study selected is a single reference image, where one or more Study Selection Rules are derived from the single reference image DICOM Parameters.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Viewport Assignment Rules contain protocols for displaying two dimensional images in the one or more Viewports.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Abstract Tags are selected from the group consisting of RelativeStudyAge, PriorIndex. NumImages, NumSeries, Num3DVolumes, Num4DSequences and Has-Report.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Viewport Assignment Rules include one or more Abstract Tags selected from the group consisting of Image Sets to be displayed, Rendering Style, Additional image sets for image fusion, Image Alignment, Colormap/Transfer Function, Slice Thickness, Zoom Factor, Camera position, Camera orientation and Labels/Overlay elements.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where the one or more Image Set Rules are selected from selection, sorting, and breaking rules, where the one or more Image Set Rules are Boolean expressions that contain parameters selected from the group consisting of DICOM parameters, abstract tags, and used-defined functions.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where in order to specify image sorting, the Image Set Rules contain an ordered list of sorting criteria.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where in order to specify image sorting, the Image Set Rules contain an ordered list of sorting criteria, where a split flag is used in order to specify image splitting.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where Abstract Tags are used in Image Set Rules.

In an embodiment of the invention, a system of displaying one or more Sets of Images from a plurality of images comprises a processor capable of selecting a primary Study from a plurality of studies, one or more digital data processors capable of carrying out the steps including applying one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying one or more Protocol Selection Rules to select a Display Protocol, where the one or more Protocol Selection Rules are based on one or more DICOM parameters and one or more Abstract Tags from the plurality of second studies, applying one or more Image Set Rules to define a plurality of Image Sets from the plurality of second studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the plurality of Image Sets based on one or more of the one or more Protocol Selection Rules, the one or more Image Set Rules, the one or more Viewport Assignment Rules, and the one or more Style Rules, where Abstract Tags are used in Image Set Rules, where an Abstract Tag identifies whether an image has already been placed into an Image Set.

In an alternative embodiment of the invention, a system of displaying one or more Sets of Images from a plurality of images comprises selecting one or more studies from a plurality of studies, one or more digital data processors for carrying out the steps including applying one or more Protocol Selection Rules to select a Display Protocol, where the one or more Protocol Selection Rules are based on one or more DICOM parameters and Abstract Tags from the plurality of studies, applying one or more Image Set Rules to define a plurality of Image Sets from the plurality of studies, applying one or more Viewport Assignment Rules to assign one or more Image Sets from the plurality of Image Sets to one or more Viewports defined in the Display Protocol, applying one or more Style Rules to define a rendering style and rendering parameters of the one or more Viewports and graphics resources for displaying the one or more Image Sets based on one or more of the Protocol Selection Rules, the one or more Image Set Rules, the one or more Viewport Assignment Rules, and the one or more Style Rules, where at least one of the one or more Viewports displays a three dimensional image.

In another alternative embodiment of the invention, a method of displaying one or more Sets of Images from a plurality of images comprises selecting a primary Study from a plurality of studies, executing on a server digital data processor a render server program which applies one or more of one or more Study Selection Rules, one or more Protocol Selection Rule, one or more Image Set Rules, one or more Viewport Assignment Rules, and one or more Style Rules to display the one or more Sets of Images including the steps of applying the one or more Study Selection Rules to generate a plurality of second studies based on one or more DICOM parameters and one or more Abstract Tags from the primary Study and one or more DICOM parameters and one or more Abstract Tags from the plurality of studies, where the plurality of second studies include the primary Study, applying the one or more Protocol Selection Rules to select a Display Protocol, where the one or more Protocol Selection Rules are based on one or more DICOM parameters and one or more Abstract Tags from the plurality of second studies, applying the one or more Image Set Rules to define a plurality of Image Sets from the plurality of second studies, applying the one or more Viewport Assignment Rules to assign one or more Image Sets from the plurality of Image Sets to one or more Viewports defined in the Display Protocol, applying the one or more Style Rules to define a rendering style and rendering parameters of the one or more Viewports and displaying the one or more Sets of Images in one or more Viewports based on one or more of the Protocol Selection Rule, the Image Set Rule, the one or more Viewport Assignment Rules, and the one or more Style Rules, where at least one of the one or more Viewports displays a volume rendered image.

In a further embodiment of the invention, a method of displaying one or more Sets of Images from a plurality of images comprises selecting a primary Study from a plurality of studies, executing on a server digital data processor a render server program which applies one or more of one or more Study selection Rules, one or more Protocol Selection Rules, one or more Image Set Rules, one or more Viewport Assignment Rules, and one or more Style Rules to display the one or more Sets of Images including the steps of applying the one or more Study Selection Rules to generate a plurality of second studies based on DICOM parameter BodyPartExamined, DICOM parameter Modality, DICOM parameter RelativeStudyAge and Abstract Tag RelativeStudyAge, Abstract Tag PriorIndex, Abstract Tag NumImages, Abstract Tag NumSeries, Abstract Tag Num3DVolumes, Abstract Tag Num4DSequences and Abstract Tag HasReport from the plurality of studies, where the plurality of second studies include the primary Study, applying the one or more Protocol Selection Rules to select a Display Protocol, where the one or more Protocol Selection Rules are based on DICOM parameter BodyPartExamined, DICOM parameter Modality, DICOM parameter HasThisSliceVolumes, DICOM parameter StudyDescription and Abstract Tags from the plurality of second studies, applying the one or more Image Set Rules to define a plurality of Image Sets from the plurality of second studies, applying the one or more Viewport Assignment Rules to assign one or more Image Sets from the plurality of Image Sets to one or more Viewports defined in the Display Protocol, applying the one or more Style Rules to define a rendering style and rendering parameters of the one or more Viewports and displaying the one or more Sets of Images in one or more Viewports based on one or more of the one or more Protocol Selection Rules, the one or more Image Set Rules, the one or more Viewport Assignment Rules, and the one or more Style Rules, where at least one of the one or more Viewports displays a post processed rendering of an image set.

In a further embodiment of the invention, a method of displaying one or more Sets of Images from a plurality of images comprises selecting a primary Study from a plurality of studies, executing on a server digital data processor a render server program which applies one or more of one or more Study selection Rules, one or more Protocol Selection Rules, one or more Image Set Rules, one or more Viewport Assignment Rules, and one or more Style Rules to display the one or more Sets of Images including the steps of applying the one or more Study Selection Rules to generate a plurality of second studies based on DICOM parameter BodyPartExamined, DICOM parameter Modality, DICOM parameter RelativeStudyAge and Abstract Tag RelativeStudyAge, Abstract Tag PriorIndex, Abstract Tag NumImages, Abstract Tag NumSeries, Abstract Tag Num3DVolumes, Abstract Tag Num4DSequences and Abstract Tag HasReport from the plurality of studies, where the plurality of second studies include the primary Study, applying the one or more Protocol Selection Rules to select a Display Protocol, where the one or more Protocol Selection Rules are based on DICOM parameter BodyPartExamined, DICOM parameter Modality, DICOM parameter HasThisSliceVolumes, DICOM parameter StudyDescription and Abstract Tags from the plurality of second studies, applying the one or more Image Set Rules to define a plurality of Image Sets from the plurality of second studies, applying the one or more Viewport Assignment Rules to assign one or more Image Sets from the plurality of Image Sets to one or more Viewports defined in the Display Protocol, applying the one or more Style Rules to define a rendering style and rendering parameters of the one or more Viewports and displaying the one or more Sets of Images in one or more Viewports based on one or more of the one or more Protocol Selection Rules, the one or more Image Set Rules, the one or more Viewport Assignment Rules, and the one or more Style Rules, where at least one of the one or more Viewports displays a post processed rendering of an image set, where the step of displaying is carried out on a client display device.

What is claimed is:
1. A method comprising:
(a) receiving at a server digital data processor from a client a primary Study of a patient selected from a plurality of studies;

(b) executing on the server digital data processor a render server program which applies a step for identifying one or more Study Selection Rules;
(c) identifying a primary condition for a first rule of the one or more Study Selection Rules;
(d) identifying a secondary condition for a second rule of the one or more Study Selection Rules, where the secondary condition selects one or more other studies for which if the one or more other studies were selected as the primary Study, then applying the primary condition to the one or more other studies would be true;
(e) applying the first rule to the primary Study, where the first rule is true for the primary Study;
(f) generating a list of a plurality of secondary studies by applying the third rule, where the secondary condition selects the plurality of secondary studies for which the second rule is true; and
(g) sending the list and instructions from the server digital data processor to the client, where the instructions are adapted to display one or more of the plurality of secondary studies.

2. The method of claim 1, where the first rule comprises IF Primary.Dicom.BodyPartExamined='bodypart'.

3. The method of claim 2, where bodypart is selected from the group consisting of abdomen, chest, and gastrointestinal tract.

4. The method of claim 2, where the second rule comprises THEN SELECT Other.Dicom.BodyPartExamined="bodypart".

5. The method of claim 4, where bodypart is selected from the group consisting of abdomen, chest, and gastrointestinal tract.

6. The method of claim 1, where the first rule comprises Primary.Dicom.Modality='mod'.

7. The method of claim 6, where mod is selected from the group consisting of computerized tomography, magnetic resonance imaging, positron emission tomography, confocal microscopes, 2D ultrasound devices, 3D ultrasound devices, computer radiography, and mammogram.

8. The method of claim 6, where the second rule comprises THEN SELECT Other.Dicom.Modality="mod".

9. The method of claim 8, where mod is selected from the group consisting of computerized tomography, magnetic resonance imaging, positron emission tomography, confocal microscopes, 2D ultrasound devices, 3D ultrasound devices, computer radiography, and mammogram.

10. The method of claim 1, where the first rule comprises IF Primary.Dicom.BodyPartExamined='bodypart' and Primary.Dicom.Modality='mod'.

11. The method of claim 10, where bodypart is selected from the group consisting of abdomen, chest, and gastrointestinal tract.

12. The method of claim 10, where mod is selected from the group consisting of computerized tomography, magnetic resonance imaging, positron emission tomography, confocal microscopes, 2D ultrasound devices, 3D ultrasound devices, computer radiography, and mammogram.

13. The method of claim 10, where the second rule comprises THEN SELECT Other.Dicom.BodyPartExamined="bodypart".

14. The method of claim 13, where bodypart is selected from the group consisting of abdomen, chest, and gastrointestinal tract.

15. The method of claim 10, where the second rule comprises THEN SELECT Other.Dicom.BodyPartExamined="bodypart" and Other.Dicom.Modality="mod".

16. The method of claim 15, where bodypart is selected from the group consisting of abdomen, chest, and gastrointestinal tract.

17. The method of claim 15, where mod is selected from the group consisting of computerized tomography, magnetic resonance imaging, positron emission tomography, confocal microscopes, 2D ultrasound devices, 3D ultrasound devices, computer radiography, and mammogram.

18. The method of claim 10, where the second rule comprises THEN SELECT Other.Dicom.BodyPartExamined="bodypart" and Other.Dicom.Modality="mod1" or Other.Dicom.Modality="mod2", where mod1 is not mod2.

19. The method of claim 18, where bodypart is selected from the group consisting of abdomen, chest, and gastrointestinal tract.

20. The method of claim 18, where mod1 and mod 2 are selected from the group consisting of computerized tomography, magnetic resonance imaging, positron emission tomography, confocal microscopes, 2D ultrasound devices, 3D ultrasound devices, computer radiography, and mammogram.

* * * * *